(12) United States Patent
Whitehurst et al.

(10) Patent No.: US 6,901,296 B1
(45) Date of Patent: May 31, 2005

(54) METHODS AND SYSTEMS FOR DIRECT ELECTRICAL CURRENT STIMULATION AS A THERAPY FOR CANCER AND OTHER NEOPLASTIC DISEASES

(75) Inventors: Todd K. Whitehurst, Santa Clarita, CA (US); James P. McGivern, Stevenson Ranch, CA (US); Janusz A. Kuzma, Parker, CO (US)

(73) Assignee: Advanced Bionics Corporation, Valencia, CA (US)

( * ) Notice: Subject to any disclaimer, the term of this patent is extended or adjusted under 35 U.S.C. 154(b) by 106 days.

(21) Appl. No.: 10/133,768

(22) Filed: Apr. 26, 2002

Related U.S. Application Data
(60) Provisional application No. 60/293,810, filed on May 25, 2001.

(51) Int. Cl.[7] .................................................. A61N 1/10
(52) U.S. Cl. ........................................................ 607/50
(58) Field of Search ........................ 607/1, 2, 50, 100; 604/20, 21; 128/898, 899

(56) References Cited

U.S. PATENT DOCUMENTS

| | | |
|---|---|---|
| 4,121,592 A | 10/1978 | Whalley |
| 4,669,475 A | 6/1987 | Turner |
| 5,193,539 A | 3/1993 | Schulman et al. |
| 5,193,540 A | 3/1993 | Schulman et al. |
| 5,312,439 A | 5/1994 | Loeb |
| 5,547,467 A | 8/1996 | Pliquett et al. |
| 5,800,493 A | 9/1998 | Stevens et al. |
| 5,919,187 A | 7/1999 | Guglielmi et al. |
| 6,021,347 A | 2/2000 | Herbst et al. |
| 6,051,017 A | 4/2000 | Loeb et al. |
| 6,115,637 A | 9/2000 | Lennox et al. |
| 6,162,219 A | 12/2000 | Nilsson et al. |
| 6,164,284 A | 12/2000 | Schulman et al. |
| 6,185,452 B1 | 2/2001 | Schulman et al. |
| 6,208,894 B1 | 3/2001 | Schulman et al. |
| 6,214,032 B1 * | 4/2001 | Loeb et al. .................... 607/1 |
| 6,366,808 B1 | 4/2002 | Schroeppel et al. |
| 6,391,026 B1 | 5/2002 | Hung et al. |
| 6,402,689 B1 | 6/2002 | Scarantino et al. |
| 6,472,991 B1 | 10/2002 | Schulman et al. |
| 2002/0026188 A1 | 2/2002 | Balbierz, et al. |
| 2002/0193859 A1 | 12/2002 | Schulman et al. |

FOREIGN PATENT DOCUMENTS

| | | |
|---|---|---|
| WO | WO-98/43700 A1 | 10/1998 |
| WO | WO-98/43701 A1 | 10/1998 |

OTHER PUBLICATIONS

Ando, et al., "Treatment of Solid Tumor by a Direct Electric Current", Japanese Journal of Cancer and Chemotherapy, vol. 26(12), (Oct. 1999), pp. 1856–1859.

Berendson, et al., "Electrochemical Aspects of Treatment of Tissue with Direct Current", European Journal of Surgery, Suppl. 574, (1994), pp. 111–115.

(Continued)

*Primary Examiner*—George Manuel
(74) *Attorney, Agent, or Firm*—Laura Haburay Bishop

(57) ABSTRACT

A small implantable stimulator(s) includes at least two electrodes for delivering electrical stimulation to surrounding tissue. The small stimulator provides means of stimulating a neoplasm with direct electrical current, such as relatively low-level direct current, without the need for external appliances during the stimulation session. The stimulator may be configured to be small enough to be implanted entirely within a neoplasm. Open- and closed-loop systems are disclosed.

26 Claims, 5 Drawing Sheets

OTHER PUBLICATIONS

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781–790.

Griffin, et al., "Low–Level Direct Electrical Current Therapy for Hepatic Metastases. I. Preclinical Studies on Normal Liver", British Journal of Cancer, vol. 72(1), (Jul. 1995), pp. 31–34.

Plesnicar, et al., "Electric Treatment of Human Melanoma Skin Lesions with Low Level Direct Electric Current: An Assessment of Clinical Experience Following a Preliminary Study in Five Patients", European Journal of Surgery, Suppl. 574, (1994), pp. 45–49.

Shi, et al., "Clinical Evaluation of Several Tumor Markers in the Diagnosis of Primary Heptic Cancer", Zhonghua Zhong Liu Za Zhi, 20(6) (Nov. 1998), pp. 437–439.

Taylor, et al., "Ablation of Neoplasia by Direct Current", British Journal of Cancer, vol. 70(2), (Aug. 1994), pp. 342–345.

Turler, et al., "Local Treatment of Hepatic Metastases with Low–Level Direct Electric Current: Experimental Results", Journal of Gastroenterology, vol. 35(3), (Mar. 2000), pp. 322–328.

Yen, et al., "Electrochemical Treatment of Human KB Cells in Vitro", Journal Bioelectromagnetics, vol. 20(1), (1999), pp. 24–41.

* cited by examiner

METHODS AND SYSTEMS FOR DIRECT ELECTRICAL CURRENT STIMULATION AS A THERAPY FOR CANCER AND OTHER NEOPLASTIC DISEASES

The present application claims the benefit of U.S. Provisional Patent Application Ser. No. 60/293,810, filed May 25, 2001, which application is incorporated herein by reference in its entirety.

FIELD OF THE INVENTION

The present invention generally relates to implantable stimulator systems and methods, and more particularly relates to implantable stimulator systems and methods utilizing one or more implantable microstimulators for direct electrical current stimulation as a therapy for cancer and other neoplastic diseases.

BACKGROUND OF THE INVENTION

In the year 2000, an estimated 1,220,100 people in the United States were diagnosed with cancer and 552,200 died of this disease. Cancer is actually a group of many related diseases, but all cancers begin with an abnormal cell. The body is made up of many types of cells. Normally, cells grow and divide to produce more cells only when the body needs them. Sometimes, however, cells keep dividing when new cells are not needed. These extra cells form a mass of tissue, called a tumor, or a neoplasm. Tumors may be benign or malignant.

1. Benign tumors are not cancer. They can often be removed and usually do not come back. Cells from benign tumors do not spread to other parts of the body. Most importantly, benign tumors are rarely a threat to life.

2. Malignant tumors are cancer. Cells in these tumors are abnormal and divide without control or order. They can invade and damage nearby tissues and organs. Also, cancer cells can break away from a malignant tumor and enter the bloodstream or the lymphatic system. That is the most common way cancer spreads from the original cancer site to form new tumors in other organs. The spread of cancer is called metastasis.

3. Leukemia and lymphoma are cancers that arise in blood-forming cells. The abnormal cells circulate in the bloodstream and lymphatic system. They may also invade or infiltrate body organs and form tumors.

Most cancers are named for the organ or type of cell in which they begin. For example, cancer that begins in the lung is lung cancer, and cancer that begins in cells in the skin known as melanocytes is called melanoma.

When cancer spreads (i.e., metastasizes), cancer cells are often found in nearby or regional lymph nodes. If the cancer has reached these nodes, then cancer cells may have spread to other organs, such as the liver, bones, or brain. When cancer spreads from its original location to another part of the body, the new tumor has the same kind of abnormal cells and the same name as the primary tumor. For example, if lung cancer spreads to the brain, the cancer cells in the brain are actually lung cancer cells. The disease is called metastatic lung cancer.

Cancer Statistics

In men, lung cancer incidence rates have reached an apparent plateau, but prostate cancer has increased dramatically. As a result, cancer of the prostate gland has become the most common type of cancer among both black (incidence rate of 163.1 per 100,000) and white (121.2 per 100,000) males. Lung cancer and colorectal cancer rates are the second and third highest, respectively, for both black and white males.

Breast cancer is by far the most common cancer among both white and black females. It occurs more frequently among white females (113.2 per 100,000) than among black females (94.0 per 100,000). Lung cancer and colorectal cancer are the second and third highest cancers, respectively, among white females compared to ranks of third and second highest, respectively, for black females. Even though lung and colorectal cancers are two of the most common cancers among females, their incidence is much lower than that for males. The fourth most common cancer for both white and black females is uterine cancer.

Treatment

Treatment for cancer can be either local or systemic. Local treatments affect cancer cells in the tumor and the area near it. Systemic treatments travel through the bloodstream, reaching cancer cells all over the body. Surgery and radiation therapy are types of local treatment. Chemotherapy, hormone therapy, and biological therapy are examples of systemic treatment. Healthy cells generally also suffer from the harmful effects of cancer treatment, which may lead to significant side effects.

Surgery includes removal of the cancer and typically some of the surrounding tissue and lymph nodes near the tumor. The side effects of surgery depend on many factors, including the size and location of the tumor, the type of operation, and the patient's general health.

Radiation therapy (a.k.a. radiotherapy) may be used instead of surgery as the primary treatment for some types of cancer. It also may be given before surgery (a.k.a., neoadjuvant therapy) to shrink a tumor so that it is easier to remove. In other cases, radiation therapy is given after surgery (a.k.a., adjuvant therapy) to destroy any cancer cells that may remain in the area. In addition, radiation may be used alone, or along with other types of treatment, to relieve pain or other problems if the tumor cannot be removed. Radiation therapy can be in either of two forms: external or internal, and some patients receive both.

External radiation comes from a machine that aims the rays at a specific area of the body, and there is no radioactivity left in the body after the treatment.

With internal radiation (also called implant radiation, interstitial radiation, or brachytherapy), the radiation comes from radioactive material in needles, seeds, wires, or catheters and placed directly in or near the tumor. Patients may stay in the hospital while the level of radiation is highest. During the hospital stay, patients may not be able to have visitors or may be limited to short visits, because patients may be immuno-compromised and prone to infection, and because visitors may be exposed to radiation. Implants may be permanent or temporary. The amount of radiation in a permanent implant goes down to a safe level before the person leaves the hospital. The doctor will advise the patient if any special precautions should be taken at home (e.g., avoiding people with infections, care of an implant wound site). With a temporary implant, there is no radioactivity left in the body after the implant is removed.

The side effects of radiation therapy depend on the treatment dose and the part of the body that is treated. Patients are likely to become extremely tired during radiation therapy, especially in the later weeks of treatment. Radiation therapy also may cause a decrease in the number of white blood cells, which are the cells that help protect the body against infection. With external radiation, there may be permanent darkening or "bronzing" of the skin in the treated area. In addition, it is common to have temporary hair loss in the treated area, and for the skin to become red, dry, tender, and itchy.

Chemotherapy is the use of drugs to kill cancer cells. One drug or a combination of chemotherapy agents may be used. Chemotherapy may be the only kind of treatment a patient needs, or it may be combined with other forms of treatment. Neoadjuvant chemotherapy refers to drugs given before surgery to shrink a tumor; adjuvant chemotherapy refers to drugs given after surgery to help prevent the cancer from recurring. Chemotherapy also may be used (alone or along with other forms of treatment) to relieve symptoms of the disease.

Chemotherapy is usually given in cycles: a treatment period (one or more days when treatment is given) followed by a recovery period (several days or weeks), then another treatment period, and so on. Most anticancer drugs are given intravenously, some are injected intramuscularly or subcutaneously, and some are given by mouth.

Sometimes the chemotherapy agents are given in other ways. For example, in an approach called intraperitoneal chemotherapy, chemotherapy agents are placed directly into the abdomen through a catheter. To reach cancer cells in the central nervous system (CNS), the patient may receive intrathecal chemotherapy, in which the chemotherapy agents enter the cerebrospinal fluid through a needle placed in the spinal column, or through a device placed under the scalp.

The side effects of chemotherapy depend mainly on the drugs and the doses the patient receives. As with other types of treatment, side effects vary from person to person. Generally, chemotherapy agents affect cells that divide rapidly. In addition to cancer cells, these include red blood cells and white blood cells. When blood cells are affected, patients are more likely to get infections, may bruise or bleed easily, may feel unusually weak and very tired. Rapidly dividing cells in hair roots and cells that line the digestive tract may also be affected. As a result, side effects may include loss of hair, poor appetite, nausea and vomiting, diarrhea, or mouth sores. Some chemotherapy agents only cause the hair to thin, while others may result in the loss of all body hair. Most side effects go away gradually during the recovery periods between treatments, and hair grows back after treatment is over. Some chemotherapy agents can cause long-term side effects such as loss of fertility.

Hormone therapy is used against certain cancers that depend on hormones for their growth, such as certain types of breast cancer and prostate cancer. Hormone therapy typically consists of drugs that are antagonists to the hormone needed to sustain the growth of the cancer cells, but this treatment may also include the use of drugs that decrease the production or enzymatic conversion of certain hormones. Another type of hormone therapy is surgery to remove organs (such as the ovaries or testicles) that make hormones.

Hormone therapy can cause a number of side effects. Patients may feel tired, have fluid retention, weight gain, hot flashes, nausea and vomiting, changes in appetite, and, in some cases, blood clots. In women, hormone therapy may cause interrupted menstrual periods and vaginal dryness. Hormone therapy in women may also cause either a loss of or an increase in fertility. In men, hormone therapy may cause erectile dysfunction, loss of sexual desire, or loss of fertility. Depending on the drug used, these changes may be temporary, long-lasting, or permanent.

Biological therapy (also called immunotherapy) helps the body's own immune system to fight cancer or to protect the body from some of the side effects of cancer treatment. Some examples of biological therapy include monoclonal antibodies, interferon (IFN), interleukin-2 (IL-2), and colony-stimulating factors (e.g., G-CSF).

The side effects caused by biological therapy vary with the specific treatment. In general, these treatments tend to cause flu-like symptoms, such as chills, fever, muscle aches, weakness, loss of appetite, nausea, vomiting, and diarrhea. Patients also may bleed or bruise easily, get a skin rash, or have swelling. These problems can be severe, but they go away after the treatment stops.

Drawbacks of available cancer treatments include damage to healthy cells and the resulting significant side effects, such as fatigue, hair loss, hormonal changes that may affect fertility and; desire, blood clots, and flu-like symptoms, and/or complex, risky, expensive surgical procedures. What is needed is a therapy for patients with cancer and other neoplastic diseases that is minimally invasive, and provides effective treatment without major side effects.

BRIEF SUMMARY OF THE INVENTION

The invention disclosed and claimed herein addresses the above and other needs and provides implantable, minimally invasive systems and methods for chronically stimulating malignant tumors and other neoplasms with low-level direct electrical current. Low-level direct electrical stimulation of neoplasms may provide significant therapeutic benefits in the treatment, control, and/or prevention of cancer and other neoplastic diseases through reduction in the volume of the neoplasm via necrosis of the neoplastic tissue. Electrical stimulation may also help trigger an immune response to a neoplasm by, for instance, indirectly releasing antigens from necrosed tissue, and perhaps directly, by causing release from cells of chemical signals that initiate, sustain, and/or amplify an immune response. In addition, this therapy may help reduce symptoms caused by the neoplasm, e.g., electrical stimulation may help control hyperthyroidism due to an excess of thyroid hormone released from a thyroid neoplasm by destroying the hormone-producing cells, i.e., the hormone supply.

A miniature implantable electrical stimulator, such as a stimulator similar to a Bionic Neuron (also referred to as a BION® microstimulator), capable of delivering a direct electric current, including a low-level direct electric current, may be implanted in a neoplasm via a minimal surgical procedure (e.g., via a small incision and through a cannula, endoscopically, etc.) for the treatment of neoplastic diseases, such as cancer. A single microstimulator may be implanted, or two or more microstimulators may be implanted to achieve direct electric current application to a larger region or for a longer period of time.

The implantable current generator capable of supplying direct current (DC) used with the present invention possesses one or more of the following properties, among other properties:

at least two electrodes for applying current to surrounding tissue;

electronic and/or mechanical components encapsulated in a hermetic package made from biocompatible material(s);

an electrical coil or the like for receiving energy and/or information inside the package, which receives power and/or data by, for instance, inductive or radio-frequency (RF) coupling to a transmitting coil placed outside the body, thus avoiding the need for electrical leads to connect devices to a central implanted or external controller;

means for receiving and/or transmitting signals via telemetry;

means for receiving and/or storing electrical power within the microstimulator; and a form factor making the microstimulator implantable via a minimal surgical procedure in a target area in the body.

The length and/or shape of the microstimulator may be varied in order to deliver more effective treatment, e.g., to treat neoplasms of different shapes and sizes. For example, the microstimulator may be a thin cylindrical device with an electrode at each end, or may be a flat circular device with two or more electrodes distributed around its periphery, or may be a spherical device with two or more electrodes distributed on its surface, or may have any size and configuration suitable for the particular treatment location and stimulation parameters.

A microstimulator may operate independently, or in a coordinated manner with other implanted microstimulators, other implanted devices, or with devices external to the patient's body. For instance, a microstimulator may incorporate sensor(s) for sensing a patient's condition, which information may be used to control electrical parameters in a closed loop manner. The sensing and stimulating capabilities may be incorporated into a single microstimulator. Alternatively or additionally, a sensor(s) may communicate sensed information to at least one microstimulator with stimulation capabilities, i.e., that can supply a direct electric current.

BRIEF DESCRIPTION OF THE SEVERAL VIEWS OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
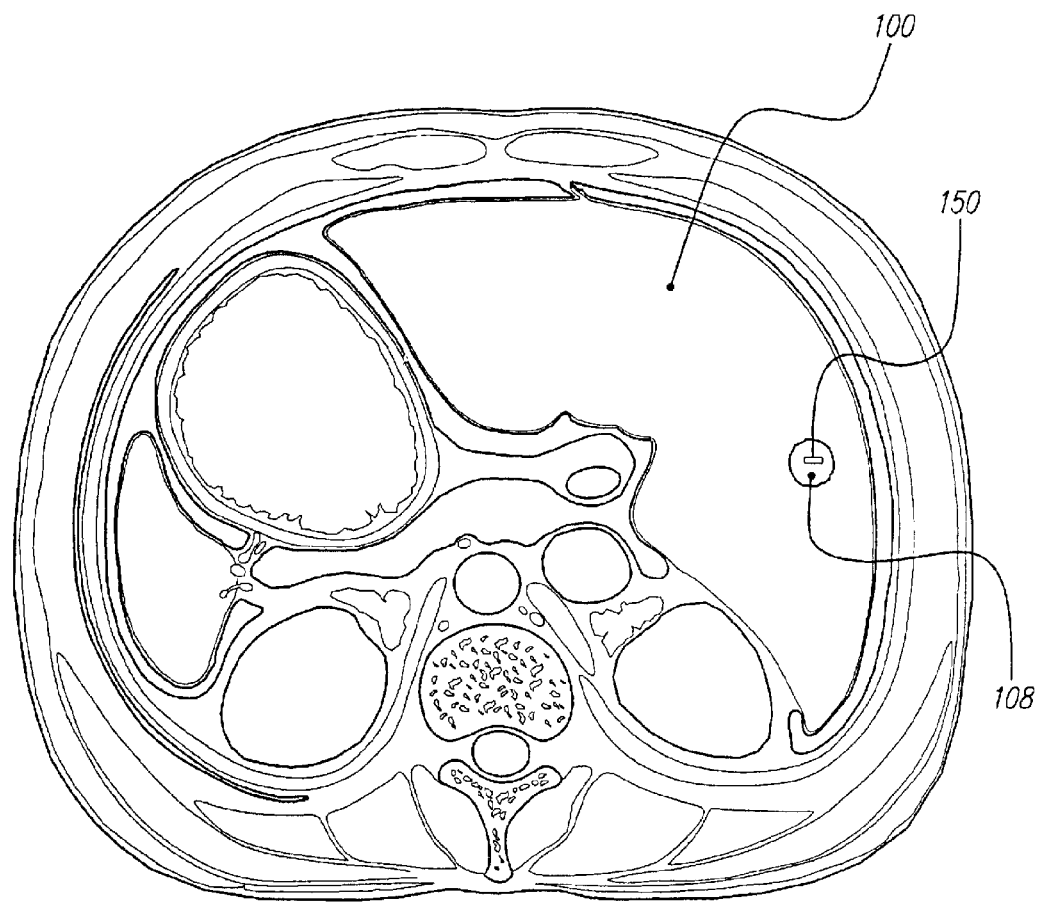
FIG. 1 is a transverse cross-section, at the level of the T12 vertebra, of the abdomen and viscera, including the liver.
Figure 2:
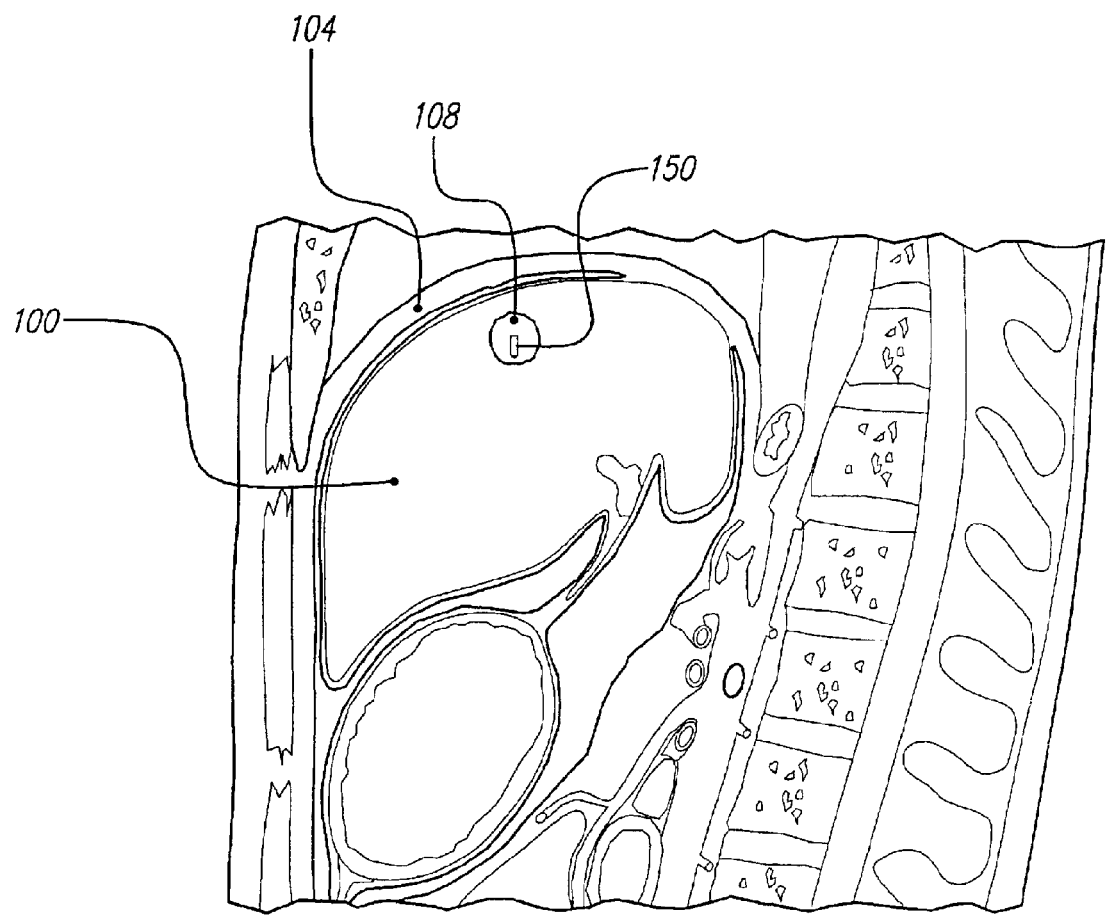
FIG. 2 is a sagittal cross-section view of the abdomen and viscera.

FIGS. 1 and 2 show a transverse cross-section view and a sagittal cross-section view, respectively, of the abdomen and viscera, including the liver. As can be seen, the liver 100 occupies the upper, right portion of the abdominal cavity, immediately below the diaphragm 104. A tumor or neoplasm 108 is depicted within liver 100. Liver 100 and liver tumor 108 of FIGS. 1 and 2 will be used to demonstrate the present invention.

Electrical Energy as Neoplasm Therapy

Low-level direct current (DC) electrical stimulation has been investigated as a means of tissue destruction, specifically as a treatment for cancer. It has various monikers in the medical literature, including direct electric current (DEC) therapy and electrochemical therapy (ECT).

A 1994 study described the primary reactions in the electrochemical treatment of tissue with direct electric current (Berendson, et al. "Electrochemical aspects of treatment of tissue with direct current" European Journal of Surgery, Suppl., 1994; (574): 111–5). The main reactions at the anode are the formation of oxygen, acidification due to liberated hydrogen ions, and, if platinum is used as anode material, the formation of chloride. At the cathode, hydrogen is formed and hydroxide ions are liberated. Based on calculations, the authors concluded that the liberated hydrogen ions determine the extents of the locally destroyed zone around the anode and that the destructive effect of chlorine probably occurs in an inner zone close to the anode.

In an article published in the journal Bioelectromagnetics, titled "Electrochemical Treatment of Human KB Cells in Vitro" (1999; 20(1): 34–41), Yen, et al. reported applying a direct electric current of 400 $\mu$A at 3 volts for 62.5 minutes to a human cancer cell culture. This resulted in 1.5 Coulombs being delivered to 5 mL of culture medium, or 0.3 Coulombs/mL. This treatment was found to delay cell growth and decrease tumor cell survival. Interestingly, using higher current and a shorter treatment time resulted in better cell survival, indicating that chronic low-level stimulation may be more effective given the same amount of charge delivery. After treatment with 400 $\mu$A at 3 volts for 208.4 minutes (i.e., 5 Coulombs in 5 mL, or 1 Coulomb/mL), the pH at the anode decreased to 4.53 and increased to 10.46 at the cathode. The effect of pH alteration on cells is thus likely one of the mechanisms of tumor cell destruction.

In 1994, Taylor, et al. studied the application of low-voltage direct electrical current in animals and humans for the ablation of benign anal condylomata acuminata (i.e., anal warts), esophageal cancer, and Kaposi's sarcoma ("Ablation of neoplasia by direct current" British Journal of Cancer, 1994 August; 70(2):342–5). A direct electric current of 20 mA applied through multiple 6 cm×1 cm, flat-plate longitudinal electrodes into the squamous mucosa of the esophagus of healthy dogs for periods ranging from 10 minutes to 2 hours resulted in necrosis of the esophageal mucosa at the site of application of the current. In humans, the application of direct electrical current to two patients with benign anal condyloma acuminata, three patients with inoperable obstructing esophageal cancer, and one patient with disseminated Kaposi's sarcoma (a skin disease commonly afflicting AIDS patients) resulted in "striking necrosis of tumor tissue" that was confirmed by macroscopic and microscopic studies.

Also in 1994, Plesnicar, et al. investigated the effects of negative low-level direct electric current electrotherapy (with an electric current of 1 mA and a treatment time of 30 minutes) in metastatic or primary melanoma skin lesions ("Electric treatment of human melanoma skin lesions with low level direct electric current: an assessment of clinical experience following a preliminary study in five patients" European Journal of Surgery, Supplement, 1994; (574): 45–9). After 12 applications in five patients, tumor regression was observed in all melanoma skin lesions; four of them were classified as partial responses. No serious side effects were observed.

Turler et al., in the article "Local Treatment of Hepatic Metastases with Low-Level Direct Electric Current: Experimental Results" (published in the Scandanavian Journal of Gastroenterology, 2000 March; 35(3): 322–8), demonstrated that low-level direct current application is an effective modality for the treatment of hepatic metastases. Using an animal model with induced cancer metastasized to the liver, direct current (80 Coulombs/cm$^3$) was applied for five weeks in the treatment group by means of one anode in the tumor center and four cathodes peripherally. In the control group, electrodes were placed without applying current. After five weeks, magnetic resonance imaging (MRI) showed a 1.6-fold tumor enlargement in the treatment group, versus a 2.9-fold enlargement in the control group. Histopathologic analysis of the treated livers yielded a 21% complete response rate and a 78% partial response rate. No necroses were found in the control group.

In 1995, Griffin, et al. also investigated the application of low-level direct electrical current to hepatic metastases in an animal model ("Low-Level Direct Electrical Current Therapy for Hepatic Metastases. I. Preclinical Studies on Normal Liver" in the British Journal of Cancer, 1995 July; 72(1): 31–4). The quantitative and qualitative relationships between electrode polarity, charge, and tissue necrosis was specifically examined. Two distinct regions of necrosis were induced, distinguishable histologically and by MRI: (i) a cylindrical region of primary necrosis centered on the electrode, its volume directly proportional to the charge passed, but greater at the anode than cathode; and (ii) a wedge-shaped infarct, apex at the electrode and base extending to the liver edge. The extent of this infarct was again greater at the anode than the cathode, but showed a sigmoidal relationship with charge. These results indicate pH changes at the electrodes as likely mediators of tissue injury, but show also that significant distant ischemic injury can occur as a consequence of primary damage.

Finally, Ando, et al. ("Treatment of Solid Tumor by a Direct Electric Current" Japanese Journal of Cancer and Chemotherapy, 1999 October; 26(12):1856–9) reported a case of a 37-year-old Japanese female with laryngeal cancer (specifically, sarcoma), which was treated by direct electric current. The patient had a complete remission, sustained for 4 years at the time of the report. Ando, et al. further reported that clinical treatment of solid tumors with direct electric current has been performed in more than 8,000 cases with complete remission in 25% of all cases and partial remission in 50%. The mechanism of action of direct electric current, however, remains unclear.

Drawbacks of available cancer treatments include damage to healthy cells and the resulting significant side effects, such as fatigue, hair loss, hormonal changes that may affect fertility and desire, blood clots, and flu-like symptoms, and/or complex, risky, expensive surgical procedures. Recently, small, implantable microstimulators have been introduced that can be implanted into soft tissues via a minimal surgical procedure. What is needed and provided herein is a therapy for patients with cancer and other neoplastic diseases that uses such a device(s), that is minimally invasive, and provides effective treatment without major side effects.

In accordance with the teachings of the present invention and as discussed in more detail presently, direct electrical current, such as a low-level direct electrical current, delivered to a neoplasm 108 is provided to treat, control, and/or prevent cancer and other neoplastic diseases. As described earlier, neoplastic diseases involve one or more abnormal benign or malignant masses of tissue. Low-level direct electrical current will likely be effective in reducing neoplastic volume through localized destruction of neoplastic tissue.

The present invention is directed to providing the treatment described herein using one or more small, implantable, electrical stimulators, referred to herein as "microstimulators". As used herein, stimulation refers to supplying a direct electrical current, including a low-level direct electrical current. Thus a stimulator or microstimulator is sometimes referred to herein as simply a stimulator, or as a current generator, and electrical current parameters are sometimes referred to herein as stimulation parameters.

The microstimulators of the present invention may be similar to or of the type referred to as BION® devices. The following documents describe various details associated with the manufacture, operation, and use of BION implantable microstimulators, and are all incorporated herein by reference:

| Application/Patent/Publication No. | Filing/Publication Date | Title |
|---|---|---|
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| U.S. Pat. No. 5,324,316 | Issued Jun. 28, 1994 | Implantable Microstimulator |
| U.S. Pat. No. 5,405,367 | Issued Apr. 11, 1995 | Structure and Method of Manufacture of an Implantable Microstimulator |
| PCT Publication WO 98/37926 | Published Sep. 3, 1998 | Battery-Powered Patient Implantable Device |
| PCT Publication WO 98/43700 | Published Oct. 8, 1998 | System of Implantable Devices For Monitoring and/or Affecting Body Parameters |
| PCT Publication WO 98/43701 | Published Oct. 8, 1998 | System of Implantable Devices For Monitoring and/or Affecting Body Parameters |
| U.S. Pat. No. 6,051,017 | Issued Apr. 18, 2000 | Improved Implantable Microstimulator and Systems Employing Same |
|  | Published September 1997 | Micromodular Implants to Provide Electrical Stimulation of Paralyzed Muscles and Limbs, by Cameron, et al., published in IEEE Transactions on Biomedical Engineering, Vol. 44, No. 9, pages 781–790. |

As will be evident to those of ordinary skill in the art upon review of the present description and of the publications listed above, the direct current (DC) blocking capacitor normally present in the circuitry of BIONs used for neurostimulation applications is removed when it is desired that the BIONs produce DC current where such current is a desired therapeutic modality, as in embodiments of the present invention.

Figure 3:
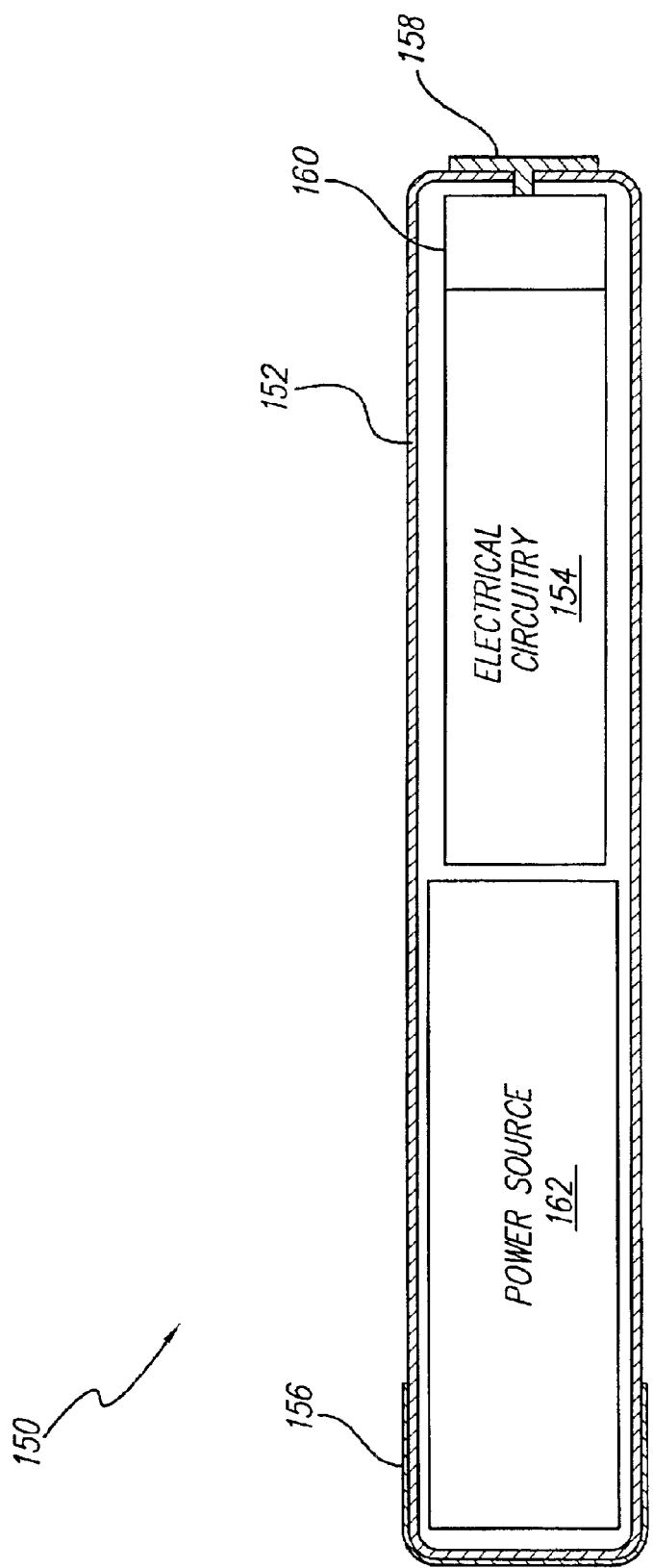
FIG. 3 is a side cross-sectional view of an exemplary embodiment of a stimulation system of the present invention.

As shown in FIG. 3, microstimulator device 150 may include a narrow, elongated capsule 152 containing electrical circuitry 154 connected to electrodes 156 and 158, which may pass through the walls of the capsule at either end. Alternatively, electrodes 156 and/or 158 may be built into and/or onto the case and/or arranged at the distal portion of a lead, as described below. As detailed in the referenced publications, electrodes 156 and 158 generally comprise a stimulating electrode (to be placed close to the target tissue) and an indifferent electrode (for completing the circuit).

Other configurations of device 150 are possible, as is evident from the above-referenced publications, and as described in more detail herein.

Certain configurations of implantable microstimulator 150 are sufficiently small to permit placement entirely within or near neoplasm 108. In accordance with the present invention, a single microstimulator 150 may be implanted, or two or more microstimulators may be implanted to achieve direct electric current application to a larger region within the neoplasm or for a longer period of time, as discussed in more detail presently.

In some such configurations, capsule 152 may have a diameter of about 4–5 mm, or only about 3 mm, or even less than about 3 mm. In these configurations, capsule length may be about 25–35 mm, or only about 20–25 mm, or even less than about 20 mm. The shape of the microstimulator may be determined by the structure of the desired target, the surrounding area, and the method of implantation. A thin, elongated cylinder with electrodes at the ends, as shown in FIG. 3, is one possible configuration, but other shapes, such as rounded cylinders, disks, spheres, and helical structures, are possible, as are different configurations of and/or additional electrodes and/or leads.

In certain embodiments of the instant invention, microstimulator 150 comprises two, leadless electrodes. However, either or both electrodes 156 and 158 (or any of the electrodes, when more than two are used) may alternatively be located at the distal portion of short, flexible leads as described in U.S. patent application Ser. No. 09/624,130 filed Jul. 24, 2000, which is incorporated herein by reference in its entirety. The use of such leads permits, among other things, electrical stimulation to be directed more locally to targeted tissue(s) a short distance from the surgical fixation of the bulk of the implantable stimulator 150, while allowing most elements of stimulator 150 to be located in a more surgically convenient site. This minimizes the distance traversed and the surgical planes crossed by the device and any lead(s). In most uses of this invention, the leads are no longer than about 150 mm, so that stimulator 150, including leads and electrodes, is contained entirely within neoplasm 108, or is located nearby. As described herein, placement entirely within or near a neoplasm includes placement of a microstimulator with, for instance, an anode located in the neoplasm, while a cathode (which electrode may be the microstimulator capsule itself) is located outside but close to the neoplasm, includes placement of anode(s) and cathode(s) within the neoplasm while the bulk of the microstimulator is located outside but close to the neoplasm, and other similar arrangements that provide the benefits of the disclosed therapy.

In addition, the length and/or shape of the microstimulator may be varied in order to deliver more effective treatment, e.g., to treat neoplasms of different shapes and sizes. For example, if the microstimulator is a thin cylindrical device with an electrode at each end, the length of this device may be varied to treat neoplasms of different sizes or shapes. As another example, if the microstimulator is a flat circular (i.e., pancake-shaped) stimulator device with two or more electrodes distributed around its periphery, the diameter of this device may be varied to treat neoplasms of different sizes. As yet another example, a substantially spherical device with two or more electrodes distributed on its surface may have any size and configuration suitable for the particular treatment location and stimulation parameters.

Microstimulator(s) 150, when certain configurations are used, may be implanted with a surgical tool such as a tool specially designed for the purpose, or may be placed, for instance, via a small incision and through a small cannula. Alternatively, device(s) 150 may be implanted via conventional surgical methods, or may be implanted using other endoscopic or laparoscopic techniques. A more complicated surgical procedure may be required for sufficient access to certain tissue, for fixing the microstimulator in place, and/or when implanting microstimulators of certain shapes.

The external surfaces of stimulator 150 may advantageously be composed of biocompatible materials. Capsule 152 may be made of, for instance, glass, ceramic, or other material that provides a hermetic package that will exclude water vapor but permit passage of electromagnetic fields used to transmit data and/or power. Electrodes 156 and 158 may be made of a noble or refractory metal or compound, such as platinum, iridium, tantalum, titanium, titanium nitride, niobium, or alloys of any of these, in order to avoid corrosion or electrolysis which could damage the surrounding tissues and/or the device.

Microstimulator 150 contains, when necessary and/or desired, electrical circuitry 154 for receiving data and/or power from outside the body by inductive, radio frequency (RF), or other electromagnetic coupling. In some embodiments, electrical circuitry 154 includes an inductive coil or other means for receiving and transmitting RF data and/or power, an integrated circuit (IC) chip for decoding and storing stimulation parameters and generating stimulation current, and additional discrete electronic components required to complete the electronic circuit functions, e.g. capacitor(s), resistor(s), coil(s), and the like.

Microstimulator 150 also includes, when necessary and/or desired, a programmable memory 160 for storing a set(s) of data, stimulation, control parameters, and/or other data, if required. Among other things, memory 160 may allow electrical and/or control parameters to be adjusted to settings that are safe and efficacious with minimal discomfort for each individual. Specific parameters may provide therapeutic advantages for various stages and forms of cancer and other neoplastic disease. For instance, some patients may respond favorably to intermittent stimulation, while others may require continuous stimulation to alleviate their symptoms.

In addition, different stimulation parameters may have different effects on different tissue. For example, decades ago, research demonstrated that monophasic waveforms are toxic to neurons, due to the build-up of charge and associated pH change in the neurons. Since then, to avoid destroying neurons, biphasic pulses have typically been used for non-toxic electrical stimulation of tissue, e.g., neurostimulation, because the second phase reverses the charge injection and effectively removes the charge from the neuron. However, in the current invention, localized destruction of neoplastic tissue via low-level direct electrical current will likely be effective in reducing neoplastic volume. The volume of tissue necrosis is likely to increase with an increasing amount of charge delivered to the tissue. In addition, a relatively lower amplitude direct electric current applied over a relatively longer treatment period may be more effective than a relatively higher amplitude direct electric current applied over a relatively shorter treatment period, even if the two treatments deliver the same amount of charge to the tissue.

In some embodiments of the current invention, electrical and control parameters are chosen to target specific tissues and to exclude others. For example, relatively low-level DC currents, e.g., less than about 100–500 $\mu A$, are likely to affect tissues very near the electrodes, i.e., within about a 34 mm radius of the electrode. Such low-level DC current may be less likely to damage vascular structures since the regular flow of blood through such structures rapidly removes toxic products, such as those created by DC currents, before they build to damaging levels.

Some embodiments of implantable current generator 150 also include a power source and/or power storage device 162. Possible power options for a current generator device of the present invention, described in more detail below, include but are not limited to an external power source coupled to current generator 150, e.g., via an RF link; a self-contained power source utilizing any suitable means of generation and/or storage of energy (e.g., a primary battery, a replenishable or rechargeable battery such as a lithium ion battery, an electrolytic capacitor, a super- or ultra-capacitor, or the like); and/or if the self-contained power source is replenishable or rechargeable, means of replenishing or recharging the power source (e.g., an RF link, an optical link, a thermal link, or other energy-coupling link).

Figure 4:
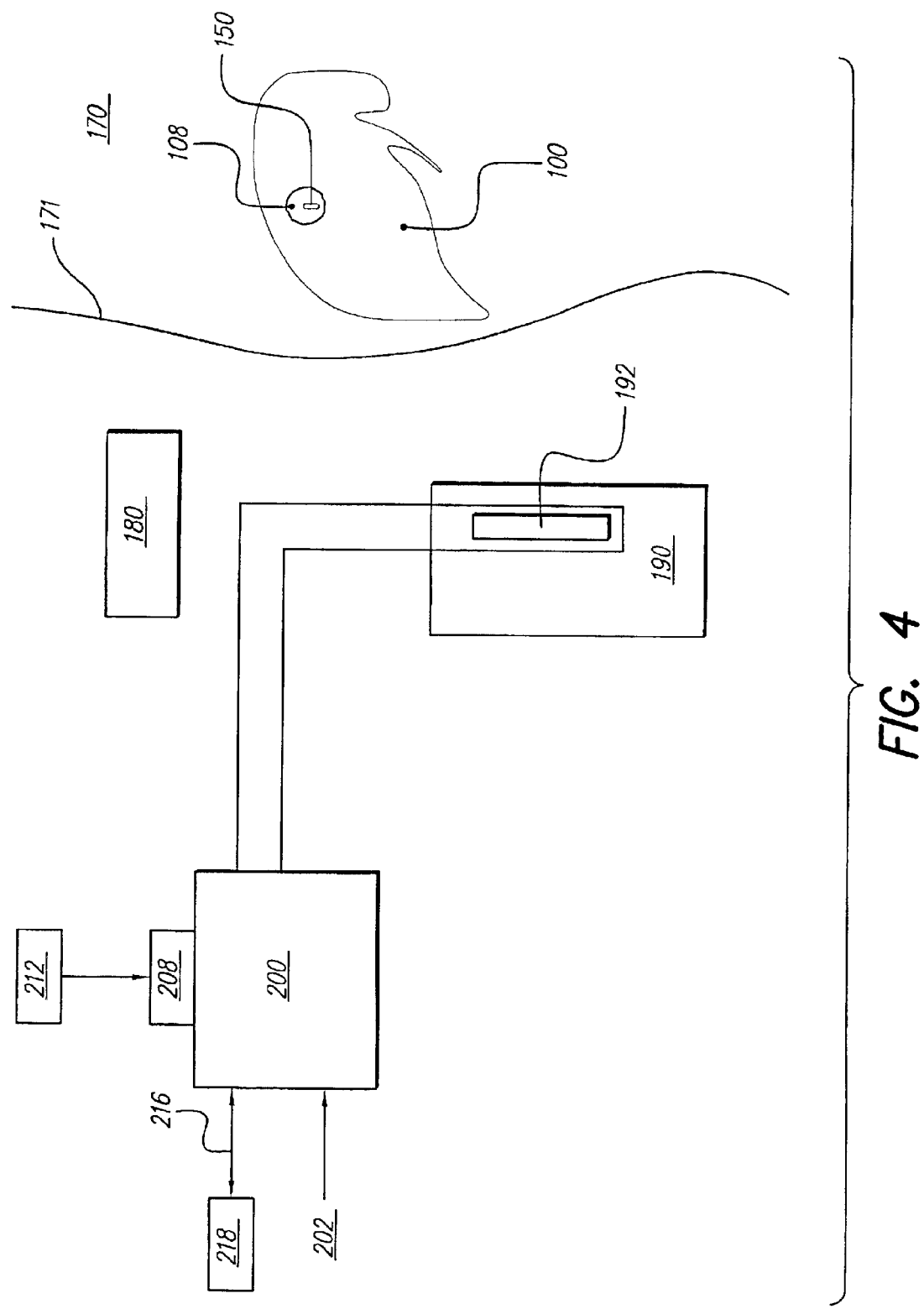
FIG. 4 illustrates exemplary external components of the invention.

In certain embodiments, and as illustrated in the exemplary embodiment of FIG. 4, the patient 170 switches stimulator 150 on and off by use of controller 180, which may be handheld. Controller 180 operates to control stimulator 150 by any of a variety of methods, including sensing the proximity of a permanent magnet located in controller 180, sensing RF transmissions from controller 180, or the like. Other methods for controlling microstimulator 150 are possible, such as an implanted button that may be pressed to activate stimulator 150.

The embodiment of FIG. 4 also depicts exemplary external components related to programming and providing power to implantable stimulator 150. When it is required to communicate with implanted current generator 150, patient 170 is positioned on or near external appliance 190, which appliance contains one or more inductive coils 192 or other means of communication (e.g., RF transmitter and receiver). External appliance 190 is connected to or is a part of external electronic circuitry appliance 200 which may receive power 202 from a conventional power source. External appliance 200 contains manual input device 208, e.g., a keypad, whereby the patient 170 or a caregiver 212 may request changes in stimulation parameters produced during the normal operation of implantable stimulator 150. In these embodiments, manual input device 208 may include various electromechanical switches and/or visual display devices that provide the patient and/or caregiver with information about the status and prior programming of implantable stimulator 150.

Alternatively or additionally, external electronic appliance 200 is provided with an interface 216 for interacting with other computing device(s) 218, such as by a serial interface cable or infrared link to a personal computer, to a telephone modem, or the like. Such interface 216 may permit a clinician to monitor the status of the implant and prescribe new stimulation parameters from a remote location.

The external appliance(s) may be embedded in a cushion, pillow, mattress cover, or garment. Other possibilities exist, including a necktie, belt, scarf, patch, or other structure(s) that may be affixed to the patient's body or clothing. External appliances may include a package that can be, e.g., worn on the belt, may include an extension to a transmission coil affixed to the body, e.g., with a velcro band or adhesive, or may be combinations of these or other structures able to perform the functions described herein.

In order to help determine the strength and/or duration of electrical current required to produce the desired effect, in some embodiments, a patient's response to and/or need for treatment is sensed. For example, microstimulator 150 may incorporate means of sensing tissue necrosis or byproducts thereof (e.g., via a pH sensor or impedance sensor), means of sensing tissue volume or indirect indicators thereof (e.g., via a pressure sensor), and/or means of sensing tissue function or indirect indicators thereof (e.g., electromyograph or EMG). Other measures of the state of the patient may additionally or alternatively be sensed, e.g., hormone, enzyme, interleukin, cytokine, lymphokine, chemokine, growth factor, neurotransmitter, ketone, electrolyte, medication or other drug levels and/or changes in these or other substances in the blood plasma or local interstitial fluid. For instance, the level or changes in level of alpha-fetoprotien (AFP), a key liver cancer tumor marker, may be sensed. Other liver cancer tumor markers may additionally or alternatively be sensed, such as alpha-L-fucosidase (AFu), gamma-glutamyltransferase (GGT), sialic acid (SA) and/or carcinoembryonic antigen (CEA). Substances may be sensed, for instance, using one or more Chemically Sensitive Field-Effect Transistors (CHEMFETs) such as Enzyme-Selective Field-Effect Transistors (ENFETs) or Ion-Sensitive Field-Effect Transistors (ISFETs, as are available from Sentron CMT of Enschede, The Netherlands).

A microstimulator may additionally or alternatively incorporate means of sensing electrical current levels supplied by another source of electrical energy. For instance, multiple microstimulators may be placed in a patient, and one stimulator may modulate its output based on the current supplied by other microstimulators. Other methods of determining a patient's response to and/or need for treatment include an iterative process whereby the physician sets the current level and then adjusts it periodically based on diagnostic imaging results and/or a patient's report of symptoms, as well as other methods mentioned herein, and yet others that will be evident to those of skill in the art upon review of the present disclosure.

For instance, in several embodiments of the present invention, a first and second "microstimulator" are provided. The second "microstimulator" periodically (e.g., once per minute) records pH (and/or AFP, oxygen level, or other indicator), which it transmits to the first stimulator. The first stimulator uses the sensed information to adjust electrical parameters according to an algorithm programmed, e.g., by a physician. For example, if the pH is close to normal (e.g., approximately 7.4), then the current is increased. In some alternatives, one "microstimulator" performs both the sensing and current generating functions, as discussed in more detail herein.

While a microstimulator may also incorporate means of sensing one or more conditions of the patient, it may alternatively or additionally be desirable to use a separate or specialized implantable device, such as an implantable pH sensor, to record and telemeter physiological conditions/responses in order to adjust stimulation parameters. This information may be transmitted to an external device, such as external appliance 190, or may be transmitted directly to implanted stimulator(s) 150. However, in some cases, it may not be necessary or desired to include a sensing function or device, in which case stimulation parameters may be fixed and/or determined and refined, for instance, by patient feedback, or the like.

Thus, it is seen that in accordance with the present invention, one or more external appliances may be provided to interact with microstimulator 150, and may be used to accomplish, potentially among other things, one or more of the following functions:

Function 1: If necessary, transmit electrical power from the external electronic appliance 200 via appliance 190 to stimulator 150 in order to power the device and/or recharge the power source/storage device 162. External electronic appliance 200 may include an automatic algorithm that adjusts stimulation parameters automatically whenever the implantable stimulator(s) 150 is/are recharged.

Function 2: Transmit data from the external appliance 200 via the external appliance 190 to the implantable stimulator 150 in order to change the operational parameters (e.g., electrical stimulation parameters) of stimulator 150.

Function 3: Transmit sensed data indicating a need for treatment or in response to stimulation from microstimulator 150 (e.g., EMG, change In pH, change in impedance, change in pressure, hormone or medication level, or other activity) to external appliance 200 via external appliance 190.

Function 4: Transmit data indicating state of the implantable stimulator 150 (e.g., battery level, stimulation settings, etc.) to external appliance 200 via external appliance 190.

By way of example, a treatment modality for a hepatic neoplasm may be carried out according to the following sequence of procedures:

1. A stimulator 150 is implanted so that it is entirely within neoplasm 108. If necessary or desired, one or more additional stimulator(s) 150 may be implanted in other areas of neoplasm 108, such as at a location near a blood vessel feeding the neoplasm. In another alternative, electrodes 156 and/or 158 are implanted in the neoplasm while the bulk of the stimulator is implanted a short distance away, near the neoplasm, e.g., in the liver.

2. Using Function 2 described above (i.e., transmitting data) of external appliance 200 and external appliance 190, stimulator 150 is commanded to produce continuous low-level DC electric current, e.g., at 100 $\mu$A.

3. Set stimulator on/off period(s) to an appropriate setting(s), e.g., one hour on then one hour off.

4. At some predefined interval, any change in pH, impedance, pressure, and/or oxygen level is sensed, for instance, by one or more electrodes 156 and 158 or sensors. These responses are converted to data and telemetered out to external electronic appliance 200 via Function 3. Alternatively, after an initial treatment period (e.g., one month), tumor size/state may be assessed by, for example, report of symptoms, ultrasound imaging, CT imaging, and/or other diagnostic imaging.

5. From the response data received at external appliance 200 from implantable stimulator 150, or from other assessment, the DC current necessary to obtain a response is determined and is used by a clinician acting directly 212 or by other computing device(s) 218 to transmit the desired DC current parameters to stimulator 150 in accordance with Function 2. For instance, the DC current setting may be increased and/or the on/off periods may be adjusted if neoplasm growth is seen on a CT scan image. Increasing DC current or stimulator on period and/or decreasing stimulator off period is likely to increase tissue degradation and/or to further slow tissue growth.

6. To cease electrical current, patient 170 employs controller 180 to turn off stimulator 150.

7. Periodically, the patient or caregiver recharges the power source/storage device 162 of implantable stimulator 150, if necessary, in accordance with Function 1 described above (i.e., transmit electrical power).

For the treatment of any of the various forms and degrees of cancer or other neoplastic disease, it may be desirable to modify or adjust the algorithmic functions performed by the implanted and/or external components, as well as the surgical approaches, in ways that would be obvious to skilled practitioners of these arts. For example, in some situations, it may be desirable to employ more than one implantable stimulator 150, each of which could be separately controlled, e.g., by a digital address. Multiple channels and/or multiple patterns of stimulation might thereby be programmed by the clinician and controlled by the patient to, for instance, stimulate larger areas of a tumor in order to maximize therapeutic efficacy.

In some embodiments, microstimulator 150, or a group of two or more microstimulators, is controlled via closed-loop operation. A need for and/or response to stimulation is sensed via microstimulator 150, or by an additional microstimulator (which may or may not be dedicated to the sensing function), or by another implanted or external device. If necessary, the sensed information is transmitted to microstimulator 150. In some embodiments, the stimulation parameters used by microstimulator(s) 150 are automatically adjusted based on the sensed information. Thus, the stimulation parameters may be adjusted in a closed-loop manner to provide stimulation tailored to the need for and/or response to stimulation.

Figure 5:
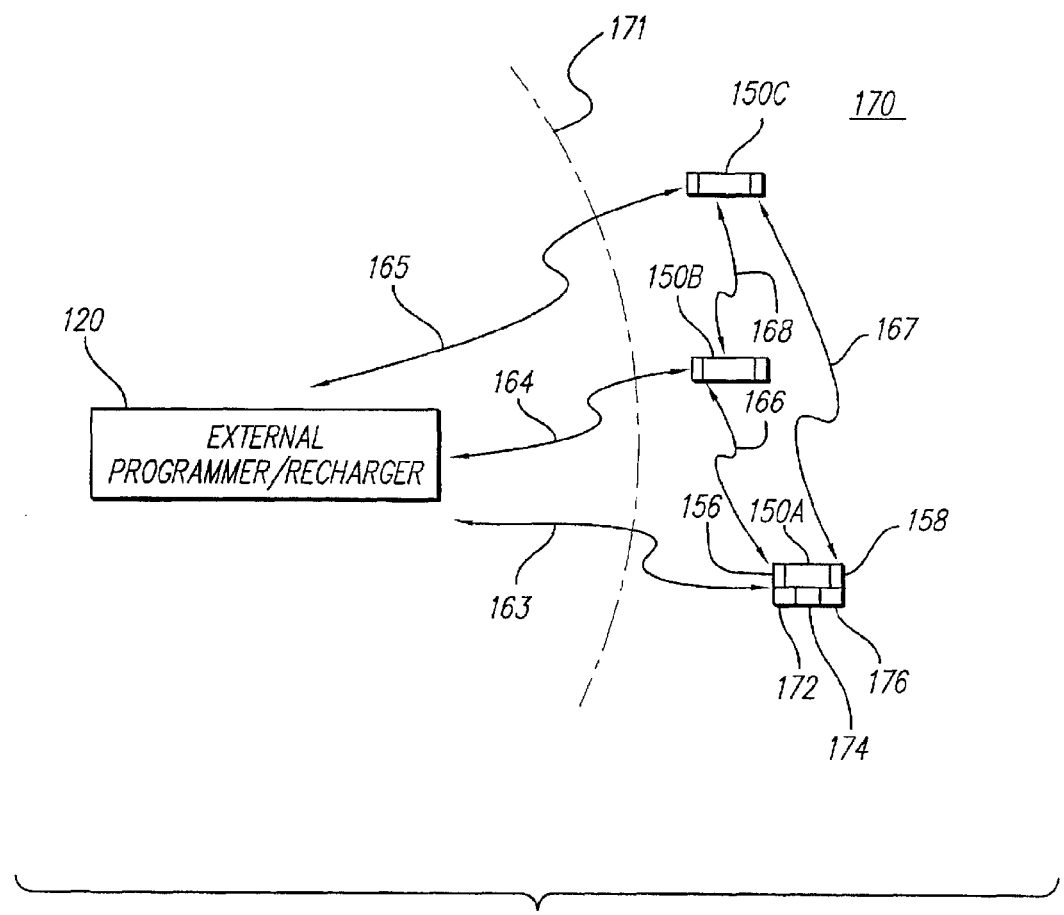
FIG. 5 depicts a system of implantable microstimulators that communicate with each other and/or with external control/programming devices.

For instance, as shown in the example of FIG. 5, microstimulator 150A, implanted beneath the skin 171 of the patient 170, provides electrical stimulation via electrodes 156 and 158 to a first location; a second microstimulator 150B provides electrical stimulation to a second location; and a third microstimulator 150C provides electrical stimulation to a third location. As mentioned earlier, the implanted devices may operate independently or may operate in a coordinated manner with other similar implanted device(s), other implanted device(s), and/or other device(s) external to the patient's body, as shown by control lines 163, 164, 165, 166, 167, and 168 in FIG. 5. That is, in accordance with various embodiments of the invention, external controller(s) 120 control the operation of each implanted device (e.g., stimulators 150A, 150B and 150C). According to certain embodiments, an implanted device, e.g., stimulator 150A, may control or operate under the control of other implanted device(s), e.g., stimulator 150B and/or 150C, or device(s) external to the patient's body, e.g., controller 120. A microstimulator made in accordance with the invention may communicate with other implanted microstimulators, other implanted devices, and/or external devices, e.g., via an RF link, an ultrasonic link, a thermal link, an optical link, or the like. Specifically, as illustrated in FIG. 5, microstimulator 150A, 150B, and/or 150C, made in accordance with the invention, may communicate with an external remote control 120 (e.g., patient and/or physician programmer) that is capable of sending commands and/or data to implanted device(s), and that may also be capable of receiving commands and/or data from implanted device(s).

A microstimulator made in accordance with certain embodiments of the invention, further incorporates a first sensor 172 for sensing therapeutic effects, clinical variables, and/or other indicators of the state of the patient, such as level(s) of or change(s) in impedance, pH, oxygen concentration, pressure, EMG, or the like, resulting from the tumor and/or from the stimulation applied to the tumor. The device may additionally or alternatively incorporate a second sensor 174 (e.g., a CHEMFET) for sensing level(s) and/or change(s) in one or more hormones, enzymes, interleukins, cytokines, lymphokines, chemokines, growth factors, neurotransmitters, ketones, electrolytes, medications or other drugs, AFP, AFu, GGT, SA, CEA, and/or other substances in the blood plasma or local interstitial fluid. The device may additionally or alternatively incorporate a third sensor 176 for sensing electrical current levels and/or waveforms supplied by another source of electrical energy.

Sensed information may be used to control electrical parameters in a closed-loop manner, as shown by control lines 166, 167, and 168. Thus, sensor(s) may be incorporated into a device that also includes electrical stimulation, or the sensor(s) (that may or may not include stimulation capabilities) may communicate the sensed information to another device(s) with stimulation capabilities. In a further alternative, one or more of the sensors may also be a stimulating electrode or other electrode. If necessary, the sensed information is transmitted to an external device, which may process the information and communicate the needed information to other internal devices providing stimulation, as shown by control lines 165, 164, and 163.

According to various embodiments of the invention, sensing and electrical stimulation are both incorporated into a single microstimulator. According to various embodiments of the invention, the sensor(s) are incorporated into at least one "microstimulator" (that may or may not be capable of stimulating), and the sensed information is, if desired, communicated to at least one other microstimulator capable of stimulating, i.e., capable of supplying a direct electric current. The implant circuitry 154 may, if necessary, amplify and transmit these sensed signals, which may be analog or digital. Information sensed by the sensor(s) may then by used to control the parameters of stimulator(s) 150 in a closed-loop manner.

According to certain embodiments of the invention, the microstimulator causes tissue necrosis and consequent reduction in the volume of the neoplasm, thereby treating patients with cancer and other neoplastic diseases and/or the symptoms thereof. Direct electric current, and more particularly, relatively low-level direct electric current (e.g., between about 0.1 mA and about 10.0 mA) is likely to produce such necrosis. (While tissue necrosis ultimately leads to reduction in volume of tissue, this therapy may cause short-term inflammation, edema, and/or swelling of the neoplasm, which may transiently increase the volume of the neoplasm.)

According to various embodiments of the invention, the electrical stimulation provided by the microstimulator causes a reduction in the rate of growth of the neoplasm and a consequent reduction in the rate of volume expansion of the neoplasm, thereby treating cancer and other neoplastic diseases. Direct electric current, and more particularly, relatively low-level direct electric current (e.g., between about 0.1 mA and about 1.0 mA) is also likely to produce such a decrease in growth rate.

Additionally, sensor(s) described earlier may be used to orchestrate first the activation of microstimulator(s) targeting one area of the tumor, and then, when appropriate, the microstimulator(s) targeting the same or another area of the tumor, in order to control symptoms, for instance, by a different means. Alternatively, this orchestration may be programmed, and not based on a sensed condition.

Additional uses of the present invention include application to reducing symptoms caused by a neoplasm. For example, this treatment may help control hyperthyroidism due to an excess of thyroid hormone released from a thyroid neoplasm. This may be effected because the therapy may decrease the activity of the neoplastic cells, e.g., may be the rate of hormone production. The destruction of the neoplastic cells, may, in turn, reduce symptoms caused by the neoplasm.

While invention herein disclosed has been described by way of specific embodiments and applications thereof, numerous modifications and variations could be made thereto by those skilled in the art without departing from the scope of the invention set forth in the claims.

What is claimed is:

1. A method for treating a patient with neoplastic disease, comprising:
   providing at least one stimulator having at least two electrodes;
   implanting the at least one stimulator in a neoplasm;
   providing operating power to the at least one stimulator;
   providing stimulation parameters to the at least one stimulator;
   generating direct electric current in accordance with the stimulation parameters; and
   delivering the current to neoplastic tissue near the at least one stimulator;
   wherein the at least one stimulator has a size and shape suitable for placement entirely within the neoplasm.

2. The method of claim 1 wherein the direct electric current is delivered at a relatively low level.

3. The method of claim 2 wherein the relatively low-level direct electric current is delivered at between about 0.1 mA and about 10.0 mA.

4. The method of claim 1 further comprising
   providing at least one sensor;
   using the at least one sensor to sense at least one physical condition; and
   providing the stimulation parameters based at least in part upon the at least one sensed condition.

5. The method of claim 4 wherein the sensed physical condition includes at least one of tissue necrosis, tissue volume, pressure, oxygen level, impedance, neurotransmitter level, change in neurotransmitter level, pH level, change in pH level, hormone level, hormone level change, enzyme level, change in enzyme level, ketone level, change in ketone level, electrolyte level, change in electrolyte level, interleukin level, change in interleukin level, cytokine level, change in cytokine level, lymphokine level, change in lymphokine level, chemokine level; change in chemokine level, growth factor level, change in growth factor level, medication level, medication level change, drug level, change in drug level, level of AFP, change in AFP level, level of AFu, change in AFu level, level of GGT, change in GGT level, level of SA, change in SA level, level of CEA, change in CEA level, EMG, level of a blood-borne substance, change in the level of a blood-borne substance, level of a local interstitial fluid, and change in the level of a local interstitial fluid.

6. The method of claim 4 wherein the at least one sensor is a part of the stimulator.

7. The method of claim 1 wherein the at least one stimulator is leadless.

8. The method of claim 7 further comprising providing and implanting more than one stimulator.

9. A microstimulator for treating a patient with neoplastic disease, comprising:
   electrical circuitry controlling electrical stimulation delivered to a neoplasm;
   at least two electrodes electrically connected to the electrical circuitry and configured to deliver the electrical stimulation to the neoplasm; and
   wherein the microstimulator is configured for implantation entirely within or near the neoplasm.

10. The microstimulator of claim 9 wherein the electrical circuitry is configured to generate direct electric current to be delivered via the electrodes at between about 0.1 mA and about 1 mA.

11. The microstimulator of claim 9 wherein the microstimulator is substantially cylindrical-shaped.

12. The microstimulator of claim 9 wherein the microstimulator is substantially pancake-shaped.

13. The microstimulator of claim 9 wherein the microstimulator is substantially spherical-shaped.

14. The microstimulator of claim 9 further comprising at least one sensor for sensing at least one physical condition.

15. The microstimulator of claim 14 further configured to control stimulation at least in part according to the at least one sensed physical condition.

16. A method for treating a patient with neoplastic disease, comprising:

providing at least one stimulator having at least two electrodes;

implanting at least one electrode of the at least one stimulator in a neoplasm;

providing operating power to the at least one stimulator;

providing stimulation parameters to the at least one stimulator;

delivering direct electric current in accordance with the stimulation parameters to neoplastic tissue near the at least two electrodes;

wherein the at least one stimulator has a size and shape suitable for placement entirely within or near the neoplasm.

17. The method of claim 16, further comprising:

providing at least one sensor;

using the sensor to sense a physical condition; and determining the stimulation parameters based at least in part upon the sensed condition.

18. The method of claim 17 wherein the at least one sensor is a part of the stimulator.

19. The method of claim 16 wherein the stimulation parameters are determined using at least one external appliance.

20. The method of claim 16 wherein the stimulation parameters are determined by the at least one stimulator.

21. The method of claim 16 wherein the stimulation parameters are fixed.

22. The method of claim 16 wherein providing power to the at least one stimulator comprises receiving power from at least one external appliance.

23. The method of claim 22 wherein providing power to the at least one stimulator further comprises storing the power received from the at least one external appliance.

24. The method of claim 16 wherein the at least one stimulator is leadless.

25. The method of claim 16 further comprising providing and implanting more than one stimulator.

26. The method of claim 16 wherein the sensed physical condition includes at least one of tissue necrosis, tissue volume, pressure, oxygen level, impedance, neurotransmitter level, change in neurotransmitter level, pH level, change in pH level, hormone level, hormone level change, enzyme level, change in enzyme level, ketone level, change in ketone level, electrolyte level, change in electrolyte level, interleukin level, change in interleukin level, cytokine level, change in cytokine level, lymphokine level, change in lymphokine level, chemokine level, change in chemokine level, growth factor level, change in growth factor level, medication level, medication level change, drug level, change in drug level, level of AFP, change in AFP level, level of AFu, change in AFu level, level of GGT, change in GGT level, level of SA, change in SA level, level of CEA, change in CEA level, EMG, level of a blood-borne substance, change in the level of blood-borne substance, level of a local interstitial fluid, and change in the level of a local interstitial fluid.

* * * * *